United States Patent [19]
Schlegel

[11] Patent Number: 5,908,938
[45] Date of Patent: Jun. 1, 1999

[54] PROCESS FOR THE PREPARATION OF 1-PHENYLPYRAZOLINE-3-CARBOXYLIC ACID DERIVATIVES

[75] Inventor: Günter Schlegel, Tokyo, Japan

[73] Assignee: Hoechst Schering AgrEvo GmbH, Berlin, Germany

[21] Appl. No.: 09/148,454

[22] Filed: Sep. 4, 1998

[30] Foreign Application Priority Data

Sep. 9, 1997 [DE] Germany ............................ 197 39 489

[51] Int. Cl.$^6$ ................................................. C07D 231/06
[52] U.S. Cl. ......................................................... 548/379.4
[58] Field of Search ........................................... 548/379.4

[56] References Cited

U.S. PATENT DOCUMENTS

| | | |
|---|---|---|
| 5,037,468 | 8/1991 | Sohn et al. . |
| 5,103,017 | 4/1992 | Sohn et al. . |
| 5,700,758 | 12/1997 | Rösch et al. . |
| 5,703,008 | 12/1997 | Rösch et al. . |

FOREIGN PATENT DOCUMENTS

| | | |
|---|---|---|
| 0409118 | 1/1991 | European Pat. Off. . |
| WO 88/06583 | 9/1988 | WIPO . |
| WO 91/07874 | 6/1991 | WIPO . |

*Primary Examiner*—Robert W. Ramsuer
*Attorney, Agent, or Firm*—Frommer Lawrence & Haug LLP

[57] ABSTRACT

There is described a process for the preparation of 1-phenylpyrazoline-3-carboxylic acid derivatives of the formula III by means of base-catalyzed reaction of hydrazones of the formula I with olefins of the formula II

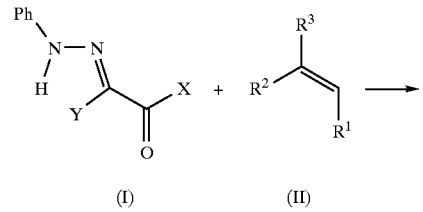

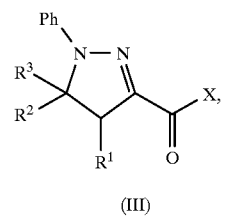

where Ph, $R^1$, $R^2$, $R^3$, X and Y have the following meanings:
Ph is optionally substituted phenyl,
$R^1$ is hydrogen or alkyl,
$R^2$ and $R^3$ independently of one another are hydrogen, halogen, cyano, an optionally substituted organic radical, or $R^2$ and $R^3$ together with the carbon atom to which they are attached form a saturated or partially saturated ring having 5 or 6 atoms,
x is amino, hydroxyl, alkoxy, cycloalkoxy, alkylamino, dialkylamino, alkyloxyalkyloxy, trialkylsilyloxy or tri-alkylsilylmethyloxy and
Y is chlorine or bromine.

The reaction is carried out in a two-phase system composed of an organic and an aqueous phase using a sterically hindered amine and, if appropriate, a further base.

These 1-phenylpyrazoline-3-carboxylic acid derivatives are employed as so-called safeners, i.e. agents which protect the useful plants in agricultural and silvicultural crops from undesired damage associated with the effect of herbicides.

12 Claims, No Drawings

PROCESS FOR THE PREPARATION OF 1-PHENYLPYRAZOLINE-3-CARBOXYLIC ACID DERIVATIVES

DESCRIPTION

The present invention relates to a process for the preparation of 1-phenylpyrazoline-3-carboxylic acid derivatives by means of base-catalyzed cycloaddition of 2-phenylhydrazone compounds with substituted olefins in a two-phase system.

Pyrazolines—like other five-membered heterocyclic compounds—can be prepared, for example, by means of [3+2]cycloaddition of unsaturated compounds with 1,3-dipolar molecules; see, for example, Jerry March, "Advanced Organic Chemistry", 3rd Ed., John Wiley & Sons, N.Y. 1985, pages 743–745, and the literature cited therein. Since a large number of 1,3-dipolar molecules are frequently not storage-stable, it is expedient to use in their place those compounds which react in situ to 1,3-dipolar molecules when exposed to bases. These reactions are usually carried out in the presence of a base with or without solvent.

WO 91/07874 has disclosed some 1-phenylpyrazoline-3-carboxylic esters as compounds which protect the useful plants in agricultural and silvicultural crops from undesired damage associated with the effect of herbicides. The synthesis described therein of 1-phenylpyrazoline-3-carboxylic esters is carried out in such a way that 2-phenylhydrazones of haloglyoxalic esters are reacted with substituted olefins with base catalysis. However, this process entails some disadvantages:

a) insufficient yield, b) insufficient purity of the product, c) high consumption of the tertiary amines employed as base, d) complicated disposal of the salt formed during the reaction of hydrogen halide and tertiary amine, e) high residue in the product of unreacted and toxicologically unacceptable 2-phenylhydrazone, f) risk of olefin polymerization under the prevailing basic conditions.

It is therefore an object of the present invention to provide a process which allows the inexpensive preparation of 1-phenylpyrazoline-3-carboxylic acid derivatives in high purity.

This aim is achieved on the basis of the known process for the preparation of 1-phenylpyrazoline-2-carboxylic acid derivatives of the formula III by means of base-catalyzed reaction of hydrazones of the formula I with olefins of the formula II

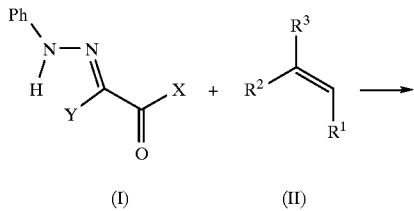

(I)  (II)

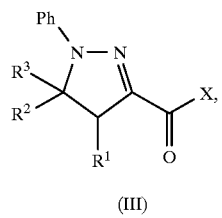

(III)

where

Ph is optionally substituted phenyl, $R^1$ is hydrogen or alkyl, $R^2$ and $R^3$ independently of one another are hydrogen, halogen, cyano, an optionally substituted organic radical, or $R^2$ and $R^3$ together with the carbon atom to which they are attached form a saturated or partially saturated ring having 5 or 6 atoms, X is amino, hydroxyl, alkoxy, cycloalkoxy, alkylamino, dialkylamino, alkyloxyalkyloxy, trialkylsilyloxy or trialkylsilylmethyloxy and Y is chlorine or bromine.

The process according to the invention thus comprises carrying out the reaction in a two-phase system in the presence of a sterically hindered amine and, if appropriate, a further base.

Preferred for the present process is the use of the above-mentioned compounds in which Ph, $R^1$ and Y are as defined above and $R^2$ and $R^3$ independently of one another are hydrogen, halogen, cyano, $C_1$–$C_6$-alkyl, $C_3$–$C_6$-cycloalkyl, $C_2$–$C_6$-alkenyl, $C_2$–$C_6$-alkynyl, halo-$C_1$–$C_6$-alkyl, $C_1$–$C_6$-alkoxy-$C_1$–$C_6$-alkyl, $C_1$–$C_6$-alkylcarbonyl, $C_1$–$C_6$-alkoxycarbonyl, $C_1$–$C_6$-alkylaminocarbonyl, di-($C_1$–$C_6$-alkyl)-aminocarbonyl, phenyl which is unsubstituted or substituted by one or more identical or different radicals selected from the group consisting of amino, carboxyl, cyano, formyl, halogen, hydroxyl, nitro, $C_1$–$C_4$-alkyl, $C_1$–$C_4$-alkoxy, $C_1$–$C_4$-alkylcarbonyl, $C_1$–$C_4$-alkoxycarbonyl, halo-$C_1$–$C_4$-alkyl, halo-$C_1$–$C_4$-alkoxy, $C_1$–$C_4$-alkylthio and $C_1$–$C_4$-alkylsulfonyl, or $R^2$ and $R^3$ together with the carbon atom to which they are attached form a saturated ring having 5 or 6 atoms, and x is amino, hydroxyl, $C_1$–$C_6$-alkoxy, $C_3$–$C_8$-cycloalkoxy, $C_1$–$C_6$-alkylamino, di-($C_1$–$C_6$-alkyl)amino, $C_1$–$C_6$-alkyloxy-$C_1$–$C_6$-alkyloxy, tri-($C_1$–$C_6$-alkyl)silyloxy and tri-($C_1$–$C_6$)silylmethyloxy.

The term "halogen" encompasses fluorine, chlorine, bromine and iodine.

An optionally substituted organic radical is optionally substituted phenyl, or alkyl, alkenyl, alkynyl, cycloalkyl, alkoxyalkyl, alkylcarbonyl, alkylaminocarbonyl, dialkylaminocarbonyl, each of which has up to 10 carbon atoms in the respective hydrocarbon radical and each of which is unsubstituted or substituted by one or more identical or different halogen atoms.

"$C_1$–$C_6$-Alkyl" is to be understood as meaning an unbranched or branched hydrocarbon radical having one, two, three, four, five or six carbon atoms, for example methyl, ethyl, propyl, 1-methylethyl, butyl, 1-methylpropyl, 2-methylpropyl, 1,1-dimethylethyl, pentyl, 2-methylbutyl, 1,1-dimethylpropyl and hexyl. Composite terms such as "$C_1$–$C_6$-alkoxy", "$C_1$–$C_6$-alkylamino" and "tri-($C_1$–$C_6$)

silyloxy", are to be understood as meaning an alkoxy, alkylamino or silyloxy group whose alkyl radicals have the meaning which corresponds in principle to the term "$C_1$–$C_6$-alkyl". "Di-($C_1$–$C_6$-alkyl)amino" means that the two alkyl radicals can be identical or different.

$C_3$–$C_8$-Cycloalkyl is cyclopropyloxy, cyclobutyloxy, cyclopentyloxy, cyclohexyloxy, cycloheptyloxy and cyclooctyloxy.

The terms "alkenyl" and "alkynyl" mean that the carbon chain can be branched or unbranched and contains at least one multiple bond, it being possible for the latter to be located in any position of the unsaturated radical in question.

Optionally substituted phenyl means that one or more hydrogen atoms of the phenyl radical are replaced by identical or different substituents selected from the group consisting of amino, carboxyl, cyano, formyl, halogen, hydroxyl, nitro, $C_1$–$C_4$-alkyl, $C_1$–$C_4$-alkoxy, $C_1$–$C_4$-alkylcarbonyl, $C_1$–$C_4$-alkoxycarbonyl, halo-$C_1$–$C_4$-alkyl, halo-$C_1$–$C_4$-alkoxy, $C_1$–$C_4$-alkylthio and $C_1$–$C_4$-alkylsulfonyl.

"Haloalkoxy" and "haloalkyl" mean that one or more hydrogen atoms are substituted by the corresponding number of identical or different halogen atoms.

A ring having 5 or 6 atoms represents a carbo- or heterocyclic radical in which up to 2 ring atoms may be from the group consisting of nitrogen, oxygen and sulfur, it being possible for this ring to be saturated or partially saturated and optionally substituted by 1 or 2 methyl groups, for example cyclopentyl, cyclohexyl, cyclohexenyl and 3-oxacyclopentyl.

In the process according to the invention, the one phase (organic phase) comprises, at the beginning of the reaction, the hydrazone (also termed component I hereinbelow), the olefin (also termed component II hereinbelow) and, if appropriate, organic solvents, while the second phase comprises water (aqueous phase). Depending on the solubility, the sterically hindered amine is dissolved in the organic and/or in the aqueous phase, while the other base is, as a rule, virtually fully dissolved or suspended in the aqueous phase. As the reaction progresses, the amount of components I and II in the organic phase declines, while the amount of compound of the formula III increases. As the amount of base in the aqueous phase declines as the reaction progresses, the amount of salt formed by the hydrogen halide originating during the reaction and the base increases in this phase.

Suitable solvents are, in principle, all organic solvents which are inert under the reaction conditions of the process according to the invention, i.e. which do not undergo undesired reactions. Especially suitable are solvents from the group consisting of aliphatic, cycloaliphatic, unsaturated aliphatic and aromatic hydrocarbons which may be chlorinated in each case, such as hexane, ligroin, petroleum ether, cyclohexane, benzene, toluene, xylene, chlorobenzene, methylene chloride, chloroform, carbon tetrachloride, ethylene chloride and trichloroethylene, aliphatic ketones such as acetones, methyl ethyl ketone, methyl isopropyl ketone and methyl isobutyl ketone, carboxylic esters such as ethyl acetate and amyl acetate, carboxamides such as N-methylpyrrolidone, dimethylformamide and dimethylacetamide, carbonitriles such as acetonitrile and propionitrile, sulfoxides such as dimethyl sulfoxide, and also sulfones such as sulfolane. Naturally, a mixture of these may also be used. Equally, the process may be carried out without organic solvent.

The molar ratio between component II and component I may be selected within a wide range and is generally 1 to 20, preferably 1 to 10, especially preferably 1 to 5. If the process according to the invention is carried out without solvents, a higher amount of component II should expediently be selected. In this case, the molar ratio between component II and component I is preferably 2 to 20, especially 2 to 10. Also, a further advantage of the process according to the invention is that in the present case the excess component II together with a sterically hindered amine may be distilled out after the end of the reaction and re-employed in a new reaction batch.

Suitable for the process according to the invention are all sterically hindered amines which are capable of binding the hydrogen halide liberated during the reaction. Especially suitable are amines from the group consisting of dialkylamines, such as diisopropylamine, trialkylamines such as triethylamine and tributylamine, dialkylbenzylamines such as N,N-dimethylbenzylamine, alkyldibenzylamines, and aromatic amines such as pyridines. They may be employed in catalytic or else at least stoichiometric amounts. Normally, they are employed in a molar ratio of 0.001 to 2, preferably 0.01 to 2, especially preferably 0.01 to 0.1, based on component I.

If the stoichiometrically hindered amine is employed in a catalytic, i.e. substoichiometric, amount, the additional use of a further base is expedient. Suitable for this purpose are those bases which are equally capable of binding the hydrogen halide liberated during the reaction. Especially suitable bases are those from the group consisting of the alkali metal carbonates and alkaline earth metal carbonates such as lithium carbonate, sodium carbonate, potassium carbonate, magnesium carbonate and calcium carbonate, alkali metal hydrogen carbonates and alkaline earth metal hydrogen carbonates such as sodium hydrogen carbonate, potassium hydrogen carbonate, magnesium hydrogen carbonate and calcium hydrogen carbonate, alkali metal hydroxides and alkaline earth metal hydroxides such as lithium hydroxide, sodium hydroxide, potassium hydroxide, magnesium hydroxide and calcium hydroxide, alkali metal acetates such as sodium acetate, and alkali metal alkoxides such as sodium methoxide, sodium ethoxide, potassium tert-butoxide. Normally, they are employed in a molar ratio of 0 to 200, preferably 0 to 100, especially preferably 10 to 100, based on sterically hindered amine. To achieve an optimal yield, the total amount of base, i.e. the amount of sterically hindered amine and further base, should be chosen to be at least sufficiently large to fully bind the hydrogen halide formed during the reaction by means of the base.

The amount of water required for carrying out the process according to the invention may also be selected within a wide range. It should be sufficiently large to be able to accommodate the salts formed during the reaction from hydrogen halide, sterically hindered amine and further base. The molar ratio between water and component II is normally in a range of 2 to 100, preferably 2 to 50. Here, the molar ratio given is based on the total amount of water employed, i.e. the amount of water introduced at the beginning of the reaction and the amount of water—comprising additional base—which is, if appropriate, added dropwise in the course of the reaction.

A special advantage of the process according to the invention is also the fact that the sterically hindered amine, which is relatively expensive, may be employed in catalytic amounts only and is continuously regenerated by the additional base, which is relatively inexpensive.

Naturally, additives such as polyethylene glycols, quaternary ammonium salts and crown ethers may be added, for example to increase the solubility of the bases.

These additives are known to those skilled in the art.

The preparation of the components I is described, for example, in WO 91/07874. As a rule, the components II are commercially available or can be prepared by methods known to those skilled in the art.

The process according to the invention is usually carried out in such a manner that the components I and II, sterically hindered amine, water and, if appropriate, organic solvent are introduced into a reaction vessel. If the sterically hindered amine is not employed in catalytic, but in at least stoichiometric, amounts, no more base is added, and the reaction mixture is brought to the reaction temperature required and stirred at this temperature. The reaction temperature required depends essentially on the reactivity of the components I and II used. It is usually between 0° and 150° C., preferably between 20° and 120° C. The process can be carried out under atmospheric pressure or under reduced pressure. If a solvent is used, care must be taken that its boiling point is at least as high as the reaction temperature required. Furthermore, care must be taken especially in the case of phase-mediating solvents such as dimethylformamide, acetone and methanol that the two-phase system of the reaction mixture is retained. If the sterically hindered amine is to be employed in catalytic amounts, a further base, which may expediently be dissolved in a suitable solvent, is added to the reaction mixture at the reaction temperatures required in such a manner that the pH of the aqueous phase of the reaction mixture is in a range between 6 and 9. The choice of suitable solvent depends essentially on the nature of the base employed. Thus, for example, water may be used for bases such as potassium carbonate and sodium hydroxide, while in the case of alkoxides it is expedient to use the alcohol on which this base is based, for example methanol in the case of sodium methoxide. The pH may be checked for example continuously by means of a pH-meter immersed in the reaction mixture, or discontinuously by sampling at brief time intervals.

The reaction, which may take approximately between 2 and 48 hours and may be monitored, for example, by thin-layer chromatography, is preferably carried out until the reaction of component I is complete. Working-up of the reaction mixture may be carried out by generally known methods such as distillation, extraction and/or filtration. The working-up method depends on the properties of the reaction mixture. As a rule, the reaction mixture can first be freed from all volatile components, such as solvents, water, sterically hindered amine and excess component II, by means of distillation. An advantage of the process according to the invention is that this distillate, which comprises amine and component II, can be used in another reaction batch. For further purification, the crude product may be extracted from the distillation residue by means of a solvent and, after the solvent has been stripped off, purified by chromatography, distillation or crystallization.

As a rule, the compounds of the formula I are obtained in higher yield and purity by the process according to the invention than by the prior art. In addition, the content of toxicologically unacceptable hydrazone of the formula I is markedly lower. Furthermore, less amine is required.

The comparison example below demonstrates the advantages of the process according to the invention over the prior art.

EXAMPLE

Preparation of diethyl 1-(2,4-dichlorophenyl)-5-methyl-2-pyrazolin-3,5-dicarboxylate (IIIa)

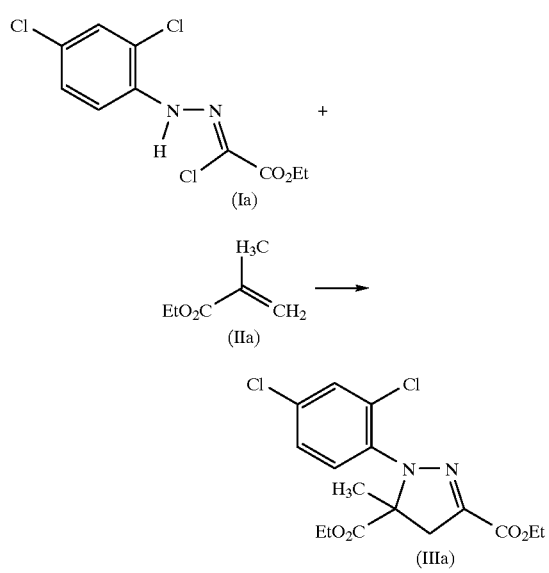

598.2 g (2 mol) of ethyl-2-chloro-(2,4-dichlorophenylhydrazono)carboxylate (Ia), 456 g (4 mol) of ethyl methacrylate (IIa) and 10.1 g (0.1 mol) of triethylamine together with 100 ml of water are introduced into a stirred flask. A solution of 195 g (1.95 mol) of potassium hydrogen carbonate in 600 ml of water is added dropwise at a temperature of 60° to 65° C. in the course of 2 hours in such a way that the pH of the aqueous phase of the reaction mixture does not exceed 8. After the dropwise addition has ended, stirring is continued for 20 minutes at the temperature given above. The excess ethyl methacrylate is distilled off in vacuo with water and triethylamine. The reaction residue is extracted with toluene. The resulting toluene extract is freed from solvent and subsequently distilled under medium high vacuum. This gives 754.2 g (98% of theory) of diethyl 1-(2,4-dichlorophenyl)-5-methyl-2-pyrazoline-3,5-dicarboxylate (IIIa) of melting point 42°–44° C. and 97% purity (determination by HPLC).

The table which follows shows the relevant reaction parameters and analytical data of the process according to the invention (experiment A) compared with the prior art (experiment B).

TABLE

| Experiment | Quantities [mole equivalents] | | | | Yield [%] | Purity [%] | Ia content [ppm] |
|---|---|---|---|---|---|---|---|
| | Component | | | | | | |
| | Ia | IIa | Base | Water | | | |
| A | 1 | 2 | 0.05 Net$_3$ + 1.0 KHCO$_3$ | 50 | 98 | 97[1)] | <5[3)] |
| B | 1 | 4 | 1.5 NEt$_3$ | 0 | 85 | 88[2)] | 900 |

[1)] Solid of melting point 42 to 44° C.
[2)] Oil of refractive index $n_D^{20}$ = 1.5651
[3)] Outside detection limit

I claim:

1. A process for the preparation of 1-phenylpyrazoline-3-carboxylic acid derivatives of the formula III by means of base-catalyzed reaction of hydrazones of the formula I with olefins of the formula II

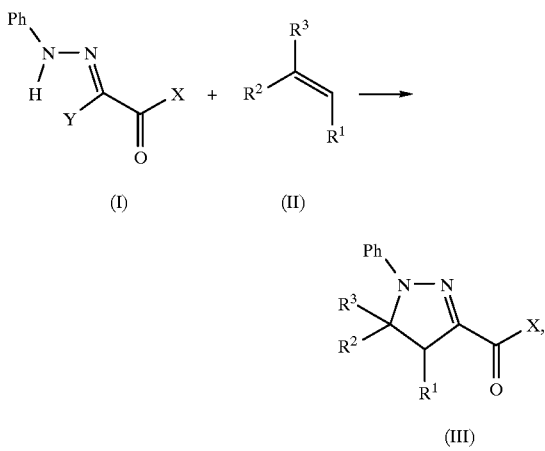

where
- Ph is optionally substituted phenyl,
- $R^1$ is hydrogen or alkyl,
- $R^2$ and $R^3$ independently of one another are hydrogen, halogen, cyano, an optionally substituted organic radical, or $R^2$ and $R^3$ together with the carbon atom to which they are attached form a saturated or partially saturated ring having 5 or 6 atoms,
- X is amino, hydroxyl, alkoxy, cycloalkoxy, alkylamino, dialkylamino, alkyloxyalkyloxy, trialkylsilyloxy or trialkylsilylmethyloxy and
- Y is chlorine or bromine, which comprises carrying out the reaction in a two-phase system, one phase being aqueous, in the presence of a sterically hindered amine and, if appropriate, of a further base.

2. The process as claimed in claim 1, wherein the one phase comprises hydrazone, olefin and, if appropriate, at least one organic solvent and the other phase comprises water.

3. The process as claimed in claim 1, wherein the sterically hindered amine is selected from the group consisting of dialkylamines, trialkylamines, dialkylbenzylamines, alkyldibenzylamines, aromatic amines, and the further base is selected from the group consisting of alkali metal carbonates, alkaline earth metal carbonates, alkali metal hydrogen carbonates, alkaline earth metal hydrogen carbonates, alkali metal hydroxides, alkaline earth metal hydroxides, alkali metal acetates and alkali metal alkoxides.

4. The process as claimed in claim 1, wherein the reaction is carried out without solvent.

5. The process as claimed in claim 1, wherein the further base is metered in in such a way that the pH of the aqueous phase of the two-phase system is within a range of between 6 and 9 at the beginning, during and at the end of the reaction.

6. The process as claimed in claim 1, wherein the reaction is carried out under atmospheric pressure or reduced pressure and at a temperature of between 25° and 120° C.

7. The process as claimed in claim 1, wherein
$R^2$ and $R^3$ independently of one another are hydrogen, halogen, cyano, $C_1$–$C_6$-alkyl, $C_3$–$C_6$-cycloalkyl, $C_2$–$C_6$-alkenyl, $C_2$–$C_6$-alkynyl, halo-$C_1$–$C_6$-alkyl, $C_1$–$C_6$-alkoxy-$C_1$–$C_6$-alkyl, $C_1$–$C_6$-alkylcarbonyl, $C_1$–$C_6$-alkoxycarbonyl, $C_1$–$C_6$-alkylaminocarbonyl, di-($C_1$–$C_6$-alkyl)-aminocarbonyl, phenyl which is unsubstituted or substituted by one or more identical or different radicals selected from the group consisting of amino, carboxyl, cyano, formyl, halogen, hydroxyl, nitro, $C_1$–$C_4$-alkyl, $C_1$–$C_4$-alkoxy, $C_1$–$C_4$-alkylcarbonyl, $C_1$–$C_4$-alkoxycarbonyl, halo-$C_1$–$C_4$-alkyl, halo-$C_1$–$C_4$-alkoxy, $C_1$–$C_4$-alkylthio and $C_1$–$C_4$-alkylsulfonyl, or $R^2$ and $R^3$ together with the carbon atom to which they are attached form a saturated ring having 5 or 6 atoms, and X is amino, hydroxyl, $C_1$–$C_6$-alkoxy, $C_3$–$C_8$-cycloalkoxy, $C_1$–$C_6$-alkyl-amino, di-($C_1$–$C_6$-alkyl)amino, $C_1$–$C_6$-alkyloxy-$C_1$–$C_6$-alkyloxy, tri-($C_1$–$C_6$-alkyl)silyloxy and tri-($C_1$–$C_6$)silylmethyloxy.

8. The process as claimed in claim 1, wherein the molar ratio between sterically hindered amine and hydrazone is 0.01 to 2 and the molar ratio between further base and sterically hindered amine is 0 to 100.

9. The process as claimed in claim 8, wherein the molar ratio between sterically hindered amine and hydrazone is 0.01 to 0.1 and the molar ratio between further base and sterically hindered amine is 10 to 100.

10. The process as claimed in claim 1, wherein the molar ratio between olefin and hydrazone is 1 to 10.

11. The process as claimed in claim 10, wherein the molar ratio between olefin and hydrazone is 1 to 5.

12. The process as claimed in claim 1, wherein the molar ratio between water and olefin is 2 to 50.

* * * * *